US010258673B2

(12) United States Patent
Pokushalov et al.

(10) Patent No.: US 10,258,673 B2
(45) Date of Patent: Apr. 16, 2019

(54) PHARMACEUTICAL COMPOSITION COMPRISING A BOTULINUM NEUROTOXIN AND USES THEREOF

(71) Applicant: Bosti Trading Ltd., Nicosia (CY)

(72) Inventors: Evgeny Pokushalov, Novosibirsk (RU); Vladislav Fomenko, Novosibirsk (RU); Nariman Salakhudinov, Novosibirsk (RU)

(73) Assignee: Bosti Trading Ltd., Nicosia (CY)

( * ) Notice: Subject to any disclaimer, the term of this patent is extended or adjusted under 35 U.S.C. 154(b) by 91 days.

(21) Appl. No.: 14/888,511

(22) PCT Filed: May 14, 2014

(86) PCT No.: PCT/IB2014/061417
§ 371 (c)(1),
(2) Date: Nov. 2, 2015

(87) PCT Pub. No.: WO2014/184746
PCT Pub. Date: Nov. 20, 2014

(65) Prior Publication Data
US 2016/0114013 A1    Apr. 28, 2016

(30) Foreign Application Priority Data
May 15, 2013 (RU) .............................. 2013122509

(51) Int. Cl.
| A61K 9/00 | (2006.01) |
| A61K 38/48 | (2006.01) |
| A61K 45/06 | (2006.01) |
| A61K 47/36 | (2006.01) |
| A61K 31/722 | (2006.01) |
| A61K 31/727 | (2006.01) |

(52) U.S. Cl.
CPC ........ *A61K 38/4893* (2013.01); *A61K 9/0019* (2013.01); *A61K 9/0024* (2013.01); *A61K 31/722* (2013.01); *A61K 31/727* (2013.01); *A61K 45/06* (2013.01); *A61K 47/36* (2013.01); *C12Y 304/24069* (2013.01)

(58) Field of Classification Search
None
See application file for complete search history.

(56) References Cited

U.S. PATENT DOCUMENTS

| 6,977,080 B1 * | 12/2005 | Donovan | A61K 31/22 |
| | | | 424/236.1 |
| 2006/0073208 A1 * | 4/2006 | First | A61K 8/64 |
| | | | 424/489 |
| 2006/0182767 A1 | 8/2006 | Borodic | |
| 2006/0228404 A1 * | 10/2006 | Anderson | A61K 9/5146 |
| | | | 424/450 |
| 2007/0037776 A1 * | 2/2007 | Richardson | A61K 9/007 |
| | | | 514/54 |
| 2010/0239667 A1 * | 9/2010 | Hemmingsen | A61K 9/2072 |
| | | | 424/466 |
| 2012/0141532 A1 | 6/2012 | Blanda et al. | |
| 2012/0238504 A1 * | 9/2012 | Moyer | A61K 8/64 |
| | | | 514/18.1 |
| 2015/0313973 A1 * | 11/2015 | Forssen | A61K 47/34 |
| | | | 424/94.67 |

FOREIGN PATENT DOCUMENTS

| JP | 06-192296 | 12/1994 | |
| JP | 2002-524527 A | 8/2002 | |
| JP | 2005306746 | * 11/2005 | ............. A61K 45/00 |
| JP | 2006-524185 A | 10/2006 | |
| JP | 2008-514353 A | 5/2008 | |
| JP | 2009-537223 A | 10/2009 | |
| RU | 2407541 C2 | 12/2010 | |
| RU | 2453333 C2 | 6/2012 | |
| RU | 2011125775 A | 2/2013 | |
| WO | WO-0015245 A2 | 3/2000 | |
| WO | WO-2004/096183 A1 | 11/2004 | |
| WO | WO-2006/005910 A2 | 1/2006 | |
| WO | WO-2006/039014 A1 | 4/2006 | |
| WO | WO-2006/046065 A1 | 5/2006 | |
| WO | WO-2007/133784 A2 | 11/2007 | |
| WO | WO-2008/000490 A1 | 1/2008 | |
| WO | WO-2010/078242 A1 | 7/2010 | |

OTHER PUBLICATIONS

Singh et al., Chitosan: A Novel Excipient in Pharmaceutical Formulation: A Review, vol. 2, Issue 9, IJPSR, 2011.*
JP-2005-306746, English translation.*
Sergeevichev, D., et al. (2018), "Globular chitosan prolongs the effective duration time and decreases the acute toxicity of botulinum neurotoxin after intramuscular injection in rats", *Toxicon*, 143: 90-95.
Park, J. et al., (2011) "Profile of Xeomin® (incobotulinumtoxinA) for the treatment of blepharospasm" Clinical Ophthalmology 5:725-732.
Pickett, A. et al., (2010) "Formulation Composition of Botulinum Toxins in Clinical Use" Journal of Drugs in Dermatology 9:9 1085-1091.
Tsuboi, M. et al., (2002) "Botulinum Neurotoxin a Blocks Cholinergic Ganglionic Neurotransmission in the Dog Heart" Jpn, J. Pharmacol 89:249-254.
Bowman, K., et al. (2006), "Chitosan nanoparticles for oral drug and gene delivery". *International Journal of Nanomedicine*, 1(2): 117-128.
Camm, J., et al. (2010), "Guidelines for the management of atrial fibrillation", *European Heart Journal*, 31: 2369-2429.
Chen, S. (2012), "Clinical Uses of Botulinum Neurotoxins: Current Indications, Limitations and Future Developments", *Toxins*, 4: 913-939.

(Continued)

*Primary Examiner* — Taeyoon Kim
*Assistant Examiner* — Srikanth Patury
(74) *Attorney, Agent, or Firm* — Harness, Dickey & Pierce, P.L.C.

(57) ABSTRACT

The invention relates a pharmaceutical composition containing botulinum toxin and a mucopolysaccharide uses thereof with increased pharmacological activity and long lasting botulinum toxin effect.

14 Claims, 5 Drawing Sheets

(56) References Cited

OTHER PUBLICATIONS

Davis, L., et al. (1984), The Co-ordination of Chitosan and Chitin Synthesis in *Mucor rouxii*, 130: 2095-2102.
Deng, C., et al. (2010), "Application of Chitosan-Based Biomaterials for Blood Vessel Regeneration", *Macromol. Symp.* 297: 138-146.
Filardo, G., et al. (2009), "New-Onset Postoperative Atrial Fibrillation After Isolated Coronary Artery Bypass Graft Surgery and Long-Term Survival", *Circ. Cardiovasc Qual Outcomes*, 2: 164-169.
Hejazi and Amiji (2002), "Polymeric Biomaterials. Second Edition, Revised and Expanded", *Anonymous*, 214.
International Search Report and Written Opinion dated Aug. 7, 2014 issued in PCT Patent Application No. PCT/IB2014/061417.
Kumar, M. (2000), "A review of chitin and chitosan applications", *Reactive & Functional Polymers*, 46: 1-27.
Linhardt, R. (2012), "Synthetic heparin", *Curr Opin Pharmacol.*, 12(2): 217-219.
Mendez, M., et al. (2012), "Role of the SNARE protein SNAP23 on cAMP-stimulated renin release in mouse juxtaglomerular cells", *Am. J. Physiol Renal Physiol*, 304: F498-F504.
Oh, S., et al. (2011), "Botulinum Toxin Injection in Epicardial Autonomic Ganglia Temporarily Supresses Vagally Mediated Atrial Fibrillation", *Circ Arrhythm Electrophysiol*, 4: 560-565.
Pokushalov, E., et al. (2014), "Botulinum Toxin Injection in Epicardial Fat Pads Can Prevent Recurrences of Artial Fibrillation After Cardiac Surgery", *Journal of the American College of Cardiology*, 64(6): 628-629.
Yogeshkumar, G., et al. (2013), "Chitosan and Its Applications: A Review of Literature", *International Journal of Research in Pharmaceutical and Biomedical Sciences*, 4(1): 312-331.

\* cited by examiner

C

D

PHARMACEUTICAL COMPOSITION COMPRISING A BOTULINUM NEUROTOXIN AND USES THEREOF

PRIORITY STATEMENT

This application is a national stage application under 35 U.S.C. § 371 of PCT International Application No. PCT/IB2014/061417 which has an International filing date of 14 May 2014, and claims priority under 35 U.S.C. § 119 to Russian Application No. 2013122509 filed 15 May 2013. The contents of each application recited above are incorporated herein by reference in their entirety.

FIELD OF THE INVENTION

The invention relates to medicine, namely to the preparation of a pharmaceutical composition comprising a botulinum neurotoxin for use in clinical practice, preferably in cardiology for the treatment of cardiac arrhythmias.

BACKGROUND OF THE INVENTION

Currently, the most commonly used botulinum neurotoxin—Botulinum neurotoxin type A (botulinum toxin type A). This neurotoxin is produced during fermentation in the presence of *Clostridium botulinum* strains.

In clinical practice, few drugs on the basis of botulinum toxin type A such as Botox (Botox), Dysport (Dysport), Kseomin (Xeomin) or Lantoks (Lantox) are used. There are a number of registered therapeutic applications for these drugs in a number of countries and there are therapeutic applications which are currently under developments and still not registered (Sheng-Chen, 2012, *Toxins Clinical Uses of Botulinum Neurotoxins: Current Indications, Limitations and Future Developments*, 4, 913-939). Documented applications by the US Food Drug Administration (FDA) include: in ophthalmology: treatment of strabismus; in neurology: treatment of blepharospasm, hemifacial spasm, spasmodic torticollis (cervical dystonia), chronic migraine (cranialgia), overactive detrusor, local muscle spasm in adults and children over 2 years old (including cerebral palsy and spasticity), axillary hyperhidrosis, hypersalivation; in aesthetic medicine: the elimination of facial wrinkles; in urology: treatment of the lower urinary tract disorders; in gastroenterology: treatment of the gastrointestinal tract disorders; in otolaryngology: treatment of spasmodic dysphonia.

Currently, the following applications of drugs based on botulinum toxin type A are under study: in dentistry: treatment of the temporomandibular joint dysfunction; in neurology: treatment of chronic musculoskeletal pain and diabetic neuropathy; in gynecology: treatment of vaginismus; in trauma and general surgery: improvement of wound healing; in cardiology: treatment of cardiac arrhythmias.

Cardiac arrhythmias are widespread and complex group of cardiac events. The only effective and rational surgical treatment of this disease is radiofrequency ablation (burning of arrhythmogenic areas of the heart using high frequency electric current). However, this method is not sufficiently effective (less than 60%) and has a high risk of complications such as hemopericardium, transesophageal fistula, post-ablation, atrial flutter, phrenic nerve paresis, mural thrombus and etc. in more than 30% of the cases (Camm et al., 2010, *Guidelines for the management of atrial fibrillation European Heart Journal*, 31, 2369-2429).

There are recent publications dedicated to the treatment of cardiac arrhythmias using botulinum neurotoxin, but the effects on the suppression of atrial fibrillation lasted no more than one week (Oh et al., 2011, *Botulinum Toxin Injection in Epicardial Autonomic Ganglia Temporarily Suppresses Vagally Mediated. Atrial Fibrillation. Circ Arrhythm. Electrophysiol.*, 4, 560-565). The duration of this effect is not acceptable in clinical practice.

Currently, manufacturers of drugs based on botulinum toxin are involved in the development of the use of stabilizing agents such as various proteins, amino acids, polysaccharides, and other components to enhance the shelf life of the toxin and its effective delivery to the target organ.

Pharmaceutical compositions comprising a botulinum neurotoxin, selected from the various serotypes A, B, C, D, E, F or G and S botulinum, and polyamine acid, selected from the group comprising polylysine, polyarginine, polyhistidine or polyornithine have been developed (patent application RU 2011125775A; WO 2010/07842).

Other pharmaceutical compositions comprising a botulinum toxin type A in an amount from 6 pg to 30 ng with a biological activity of approximately 50-250 Units of $LD_{50}$ (Lethal Dose, 50%), and additional components, such as buffer pH, excipient, diluent, cryoprotective agent and/or a stabilizer, selected from of hyaluronic acid, polyvinylpyrrolidone or polyethylene glycol have been developed (patent RU 2453333 C2, WO 2008/000490).

However, those known compositions do not have a prolonged action, nor increase the therapeutic effect of botulinum toxin and are not intended to treat cardiac arrhythmias. Those formulations have insufficient exposure in the tissues of the heart for optimal effect, and might have the rapid elimination of the active substance into the systemic circulation.

A liquid pharmaceutical composition comprising: (a) botulinum neurotoxin complex (type A, B, C, D, E, F or G) or high purity botulinum neurotoxin (type A, B, C, D, E, F or G) at concentration from 50 to 10,000 units $LD_{50}$ per 1 ml solution, (b) a stabilizing agent comprising a surfactant (SAS), preferably polysorbate 80 in an amount from 0.005 to 0.02 vol. %, (c) sodium chloride as a crystalline agent in a concentration from 0.15 to 0.3 M, (d) a disaccharide, preferably sucrose, at a concentration 10-20 mM, (d) a buffer, mainly histidine, to maintain the pH 5.5-7.5 and water has been also developed (patent RU 2407541 C2, WO 2006/005910). However, those known compositions are not intended to treat disorders of cardiac rhythm, and there are said to induce stabilizing effects on botulinum toxin without any indications or suggestion of any prolonging action, or reduction of the therapeutic dose and side effects.

Therefore, there are important needs for new strategies of treatment of cardiac arrhythmias, in particular atrial fibrillation, which would lead to durable effects and would limit the potential side effects.

SUMMARY OF THE INVENTION

The invention relates pharmaceutical compositions of botulinum neurotoxins useful for treating cardiac arrhythmia, in particular having a high therapeutic effect, an increased lasting effect and reduced side effects.

The Applicant has unexpectedly discovered that compositions of the invention achieves increased pharmacological activity of the botulinum toxin type A, a desired therapeutic effect already achieved by a single dose, a prolongation of the botulinum toxin effect, while a reduction of botulinum toxin side effects. Further, compositions of the invention allow preparing compositions with the desired properties for personalized medicine directly into the clinic and present a prolonged activity when maintained in the solution ready to the introduction.

A first aspect of the invention provides a composition containing botulinum toxin, in particular botulinum toxin type A, and a mucopolysaccharide selected from the group consisting of chitosan and nadroparin, taken in a weight ratio of 1:from $10^3$-$10^9$), preferably 1:(from $10^6$-$10^8$), and a pharmaceutically acceptable excipient with the following components:

| botulinum toxin | 1-200 U/ml |
| mucopolysaccharide | 0.1-50 mg/ml |
| saline | 0.1-50 ml. |

A second aspect of the invention relates to a pharmaceutical formulation according to the invention for use as a medicament.

A third aspect of the invention relates a use of a composition according to the invention for the preparation of a pharmaceutical preparation for the prevention and/or treatment of cardiac arrhythmias, in particular atrial fibrillation or arterial hypertension.

A fourth aspect of the invention relates to a method of preventing and/or treating cardiac arrhythmias, in particular atrial fibrillation, or arterial hypertension in a subject in need thereof, such method comprising administering a pharmaceutical formulation according to the invention in said subject.

A fifth aspect of the invention relates to a medicinal kit comprising in compartmental form a first compartment or series of compartments comprising a composition according to the invention and a second compartment or series of compartments comprising a syringe for injection with instructions for use.

A sixth aspect of the invention relates to medicinal kit for the preparation of a composition according to the invention, comprising in compartmental form a first compartment or series of compartments comprising a botulinum toxin solution and a second compartment or series of compartments comprising a chitosan powder and optionally a vial for formulation preparation with instructions for use.

DETAILED DESCRIPTION

Figure 1:
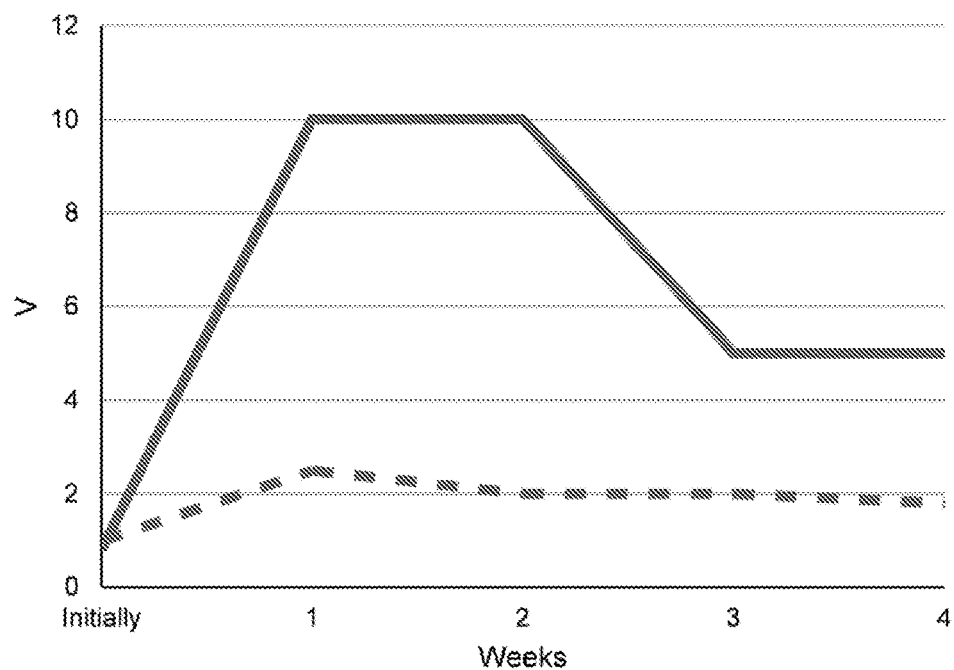
FIG. 1 represents the effect of pharmaceutical compositions of the invention as represented by the change in the electrostimulation threshold (measured in Volts) of rat's femoral muscles as compared to a commercial formulation (Xeomin) and to comparative formulations comprising botulinum toxin and another mucopolysaccharide, as described in Example 9. A: Formulation No 2 (—Chitosan); B: Formulation No 6 (—Nadroparin); C: Comparative formulation No 11 (—Sodium hyaluronate); D: Comparative formulation No 4 (—Heparin); (—) Xeomin.
Figure 1:
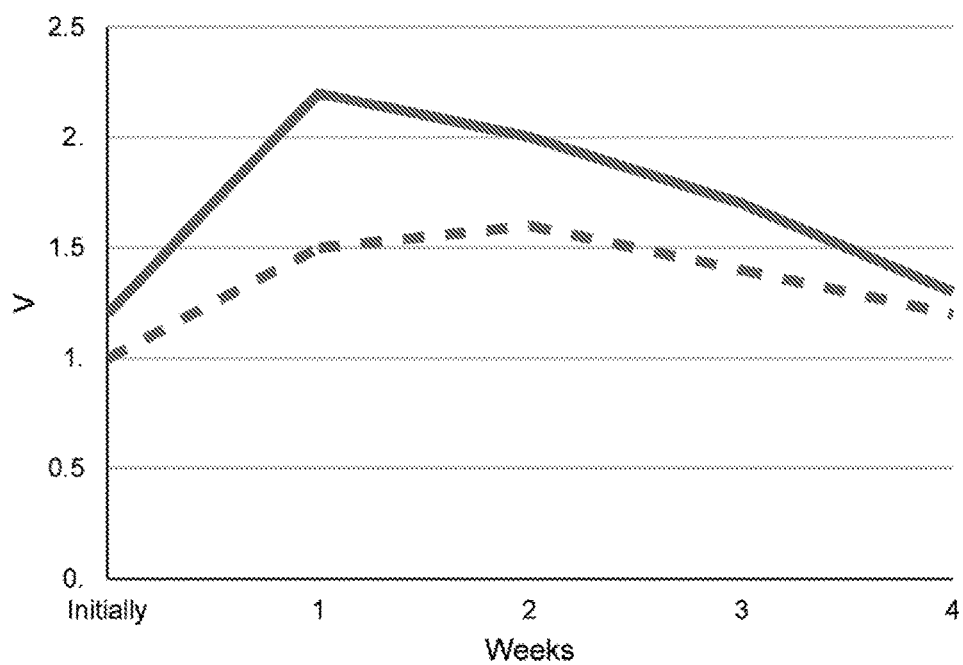
Figure 1:
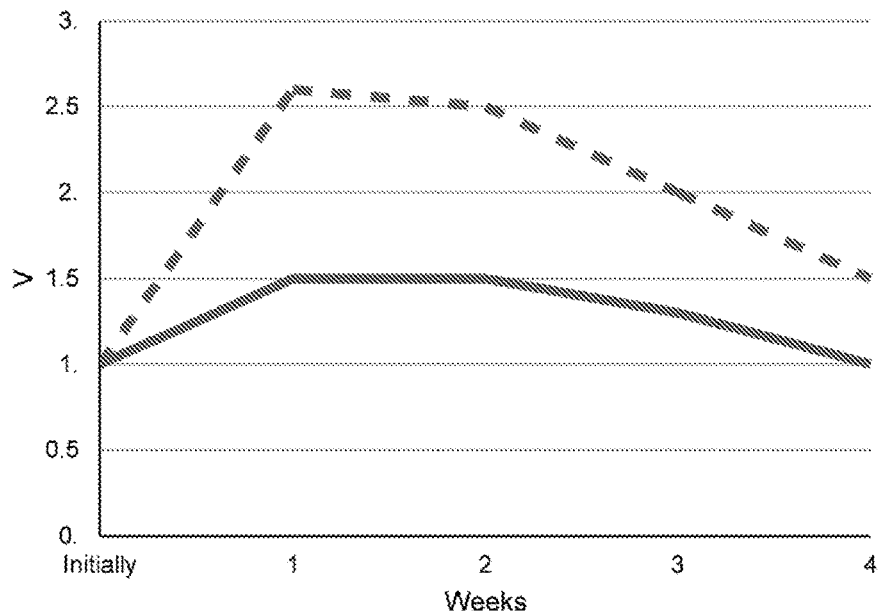
Figure 1:
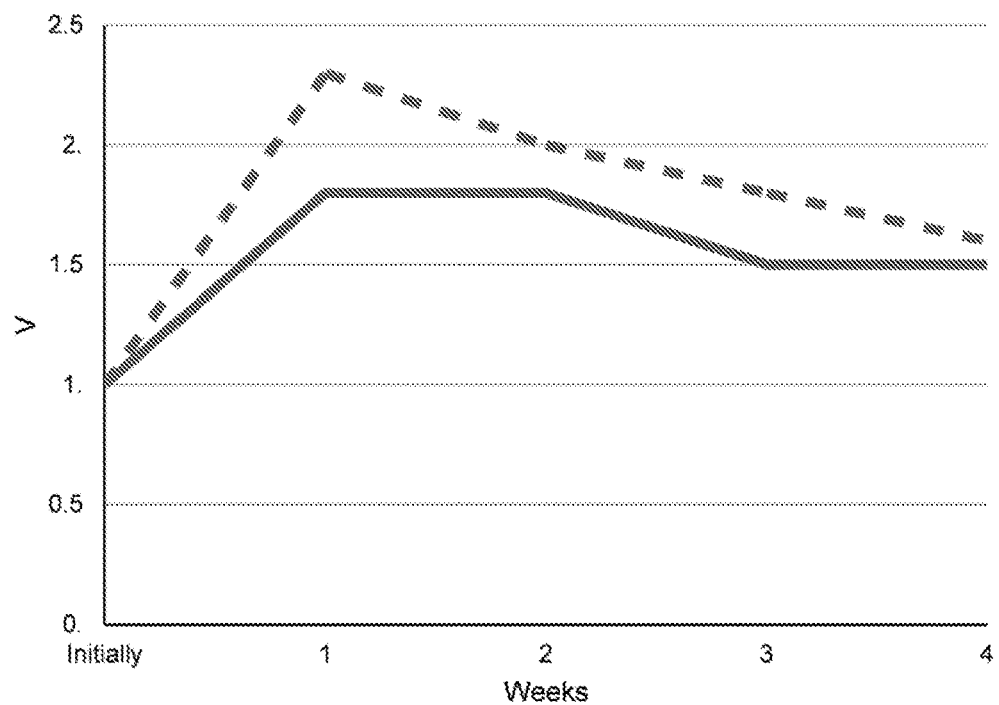

The term "Botulinum toxin" refers to any type of Botulinum toxin selected from the types A, B, E, F and G. Botulinum toxin (BTX) acts by blocking the release of acetylcholine from the presynaptic terminal of the neuromuscular junction. Seven distinct antigenic botulinum toxins (BTX-A, B, C, D, E, F, and G) produced by different strains of *Clostridium botulinum* have been described. The human nervous system is susceptible to 5 toxin serotypes (BTX-A, B, E, F, G) and unaffected by 2 (BTX-C, D). Botulinum neurotoxins are produced as inactive polypeptides of 150 kDa, which are cleaved by trypsin-like bacterial protease to generate the di-chain active form of the toxin. The proportion of single to di-chain toxin is dependent on the toxin's serotype and whether or not the bacterial strain expresses the appropriate protease. The 100-kDa heavy (H) chains and the 50-kd light (L) chains are linked together by heat-labile disulfide bonds and noncovalent forces. The H and L chains dissociate with heat and boiling, which inactivates the toxin because neurotoxicity requires both H and L chains.

The term "botulinum toxin type A" refers to any commercially available products based on botulinum toxin type A which can be used according to the invention, for example, "BOTOX™", "Dysport™", "Kseomin™", "Lantoks™", etc.

Botulinum toxin serotype A has typically a molecular weight of about 150 kDa and is a protein in the form of double-chain polypeptide consisting of the heavy chain and light chain which are connected by a disulfide bridge. In humans heavy chain causes fixing with presynaptic cholinergic nerve terminals and cellular uptake of the toxin. The light chain is believed to be responsible for the toxic effects, acting as zinc-endopeptidase and splitting specific proteins responsible for membrane fusion. Disrupting the process of membrane fusion within the cell, botulinum toxin prevents the release of acetylcholine in the synaptic cleft. The full effect of botulinum toxin in the neuromuscular transmission interrupts neuromuscular transmission and in fact denervates muscles. Botulinum toxin also has an activity in other peripheral cholinergic synapses, causing the decrease in salivation and sweating. Botulinum toxin serotype A can be obtained by purification and isolation from bacterium *Clostridium botulinum* culture such as described in U.S. Pat. No. 7,189,541 (Botulinum toxin production method); U.S. Pat. No. 6,818,409 (Isolation and purification of *Clostridium botulinum* toxins) or recombinantly produced as described in U.S. Pat. No. 6,967,088 (Soluble recombinant botulinum toxin proteins).

The term <<chitosan>> refers to as a chitin derivatives obtained by partial to substantial alkaline N-deacetylation of chitin also named poly(N-acetyl-D-glucosamine), which is a naturally occurring biopolymer that can be extracted from extracted from the shells of crustaceans, such as shrimp, crab and other sea crustaceans, including *Pandalus borealis* and cell walls of fungi such as for example described in Kumar, 2000, *reactive and Functional Polymers*, 46(1), 1-27 and Yogeshkumar, 2013, *International Journal of Research in Pharmaceutical and Biomedical Sciences*, 4(1), 312-331; Davis et al., 1984, *J. Gen. Microbiol.*, 130(8):2095-102.

Chitosan, as a natural material, has been widely investigated in this field due to its structural similarity to glycosaminoglycans (GAGs), which are the components of the extracellular matrix (ECM). Chitosan, the partially deacetylated derivative of chitin, is a linear polysaccharide, composed of glucosamine and N-acetyl glucosamine units linked by $\beta$ (1-4) glycosidic bonds. By their structures chitosans are similar to a polymer lining vascular intima and has fully biocompatibility with human tissues, characterized by low toxicity (Chao Deng et al., 2010, *Macromol. Symp.*, 297, 138-146).

According to a particular embodiment, chitosans of the invention are of crab shell origin and are obtained after a mechanical comminution and a deacetylation process.

According to another particular embodiment, chitosans of the invention have a deacetylation degree of about 85% to about 100%.

According to another particular embodiment, chitosans of the invention have an average molecular weight (Mw) of about 100 kDa to about 1,000 kDa.

The term "Heparin" refers to a mucopolysaccharide having anticoagulant direct action and has a molecular weight comparable to molecular weight of botulinum toxin. It can be extracted from crushed bovine lung or recombinantly produced as described in Linhardt et al., 2012, *Curr. Opin. Pharmacol.*, 12(2): 217-219.

The term "Nadroparin" refers to a mucopolysaccharide having anticoagulant direct action and is a low-molecular heparin with a molecular weight of more than an order of magnitude less than that of botulinum toxin. It can be isolated from mammalian tissue (U.S. Pat. No. 2,884,358 or Synthesized from UDP-sugar precursors as a polymer of alternating D-glucuronic acid and N-acetyl-D-glucosamine residues (Hazardous Substances Data Bank (HSDB®).

Compositions

The invention provides pharmaceutical compositions and methods for treating a subject, in particular a mammalian subject, and most particularly a human patient who is suffering from cardiac arrhythmias, in particular atrial fibrillation or a risk of developing cardiac arrhythmias, in particular atrial fibrillation.

In a particular embodiment, the invention provides pharmaceutical compositions of the invention for use as a medicament.

Pharmaceutical compositions of the invention may further comprise one or more pharmaceutically acceptable additional ingredient(s) such as stabilizers, antimicrobial agents, buffers, coloring agents, adjuvants, and the like.

The compositions according to the invention, together with a conventionally employed adjuvant, carrier, diluent or excipient may be placed into the form of pharmaceutical compositions and unit dosages thereof, and in such form may be employed as solids, such as implants or filled capsules, or liquids such as solutions, suspensions, emulsions, elixirs, or capsules filled with the same, in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. According to a particular embodiment, compositions according to the invention are injectable.

Further materials as well as formulation processing techniques and the like are set out in Part 5 of Remington's "*The Science and Practice of Pharmacy*", 22nd Edition, 2012, University of the Sciences in Philadelphia, Lippincott Williams & Wilkins the content of which is incorporated herein by reference.

According to one aspect, for the pharmaceutically acceptable excipient, saline is preferably used (e.g. 0.9% sodium chloride). The compositions of the invention may optionally include, additional components, such as pH buffering agent, excipient, diluent cryoprotective agent and/or stabilizer.

According to one aspect, compositions of the invention comprise composition according to any one of claims 1 to 4 wherein the weight ratio of botulinum neurotoxin, in particular Botulinum toxin A, to mucopolysaccharide is from about $1:1.5 \times 10^7$ to about $1:5 \times 10^7$, for example $1:4.4 \times 10^7$.

According to another aspect, compositions of the invention comprise composition according to any one of claims 1 to 4 wherein the weight ratio of botulinum neurotoxin, in particular Botulinum toxin A, to mucopolysaccharide is from about $1:1.5 \times 10^7$ to about $1:5 \times 10^7$, for example $1:76 \times 10^7$.

According to one aspect, compositions of the invention comprise a dosage of about 20 to about 200 UI of Botulinum toxin (typically 50 UI), in particular Botulinum toxin A, for 1 injection procedure.

According to another aspect, compositions of the invention are in the form of a dosage of injection procedure volumes of 2,000 µL.

Mode of Administration

Compositions of this invention may be administered in any manner including, in particular, in the epicardiac area (notably in the visible area of the major epicardiac fat pads) in case of treatment atrial fibrillation. In certain embodiments, a combination of different administration routes may also be used. Methods such as intramyocardial administration by injection endovascular catheters, intravascular infusion into the artery that feeds the target organ (heart, kidney) can be used for the administration of compositions of the invention.

The exact dose of the composition compositions is readily determined by one of skill in the art depending upon a variety of factors, including pharmacokinetic properties, patient conditions and characteristics (sex, age, body weight, health, size), extent of symptoms, concurrent treatments, frequency of treatment and the effect desired.

Figure 6:
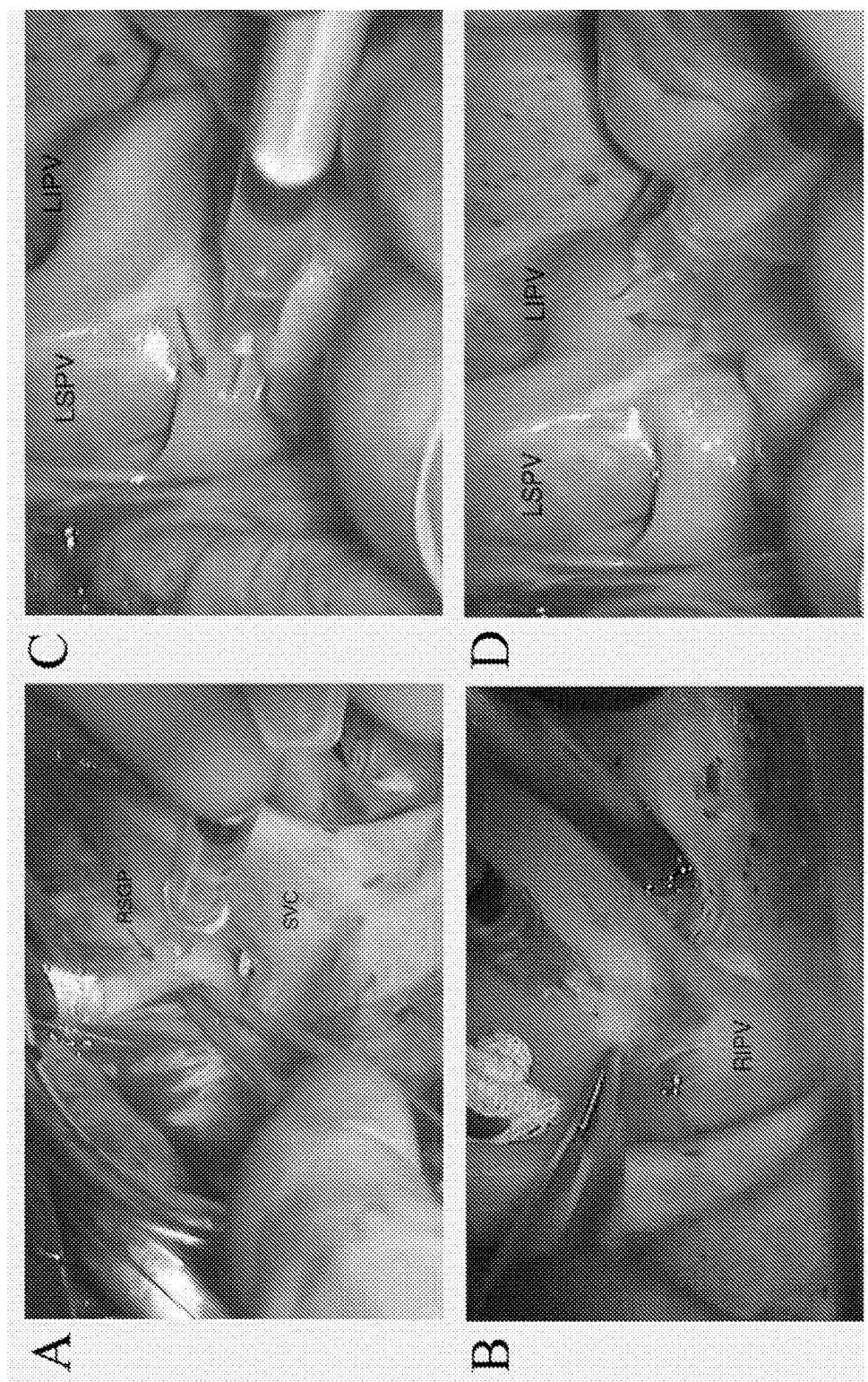
FIG. 6 shows an example of administration of a composition of the invention into the visible area of the four major epicardial fat pads. A: The first epicardial left atrial fat pad is located anterior to the right superior pulmonary vein (PV) and corresponded to the anterior right ganglionated plexus (GP); B: the second epicardial fat pad is located inferoposterior to the right inferior pulmonary vein and corresponded to the inferior right GP; C: the third fat pad is located anterior to the left superior PV and left inferior PV (between the PVs and left atrial appendage (LAA)) and corresponded to the Marshall tract GP and superior left GP; and D: the fourth fat pad is located inferiorly to the left inferior PV and extended posteriorly and corresponded to the inferior left GP. The needle tip is positioned manually at several points on the epicardial surface of the fat pads under direct visual control to ensure optimal injection.

According to one embodiment, compositions of the invention are administered before or at the beginning of the coronary artery bypass graft surgery. According on one embodiment, after the main stage of the surgery, compositions of the invention is injected into the entire visible area of the four major epicardial fat pads (such as illustrated on FIG. 6).

According to a further embodiment, compositions of the invention are administered at a botulinum toxin dose of about 50 U/1 mL in at least one in at least one epicardial fat pad, preferably in at each fat pad.

Combination

According to the invention, pharmaceutical formulations of the invention can be administered alone or in combination with a co-agent useful in the prevention and/or treatment of cardiac arrhythmias, in particular atrial fibrillation or arterial hypertension e.g. for example a co-agent selected from an antiarrhythmic substance of I, II, III classes (such as procainamide, amidaron, sotalol).

The invention encompasses the administration of a pharmaceutical formulation to an individual prior to, simultaneously or sequentially with other therapeutic/prophylactic regimens or co-agents in the prevention or treatment of cardiac arrhythmias, in particular atrial fibrillation or arterial hypertension (e.g. combined regimen), in a therapeutically effective amount. A pharmaceutical formulation that is administered simultaneously with said co-agents can be administered in the same or different composition(s) and by the same or different route(s) of administration.

Patients

In an embodiment, patients according to the invention are patients suffering from a disorder selected from cardiac arrhythmia, in particular atrial fibrillation, and arterial hypertension.

In another embodiment, patients according to the invention are patients at risk of suffering from a disorder selected from cardiac arrhythmia, in particular atrial fibrillation, for example patients undergoing coronary artery bypass graft (CABG) surgery, heart valve surgery or other open heart surgery, which are associated with a 30% risk of atrial fibrillation in the early postoperative period (Filardo et al., 2009, *Circ. Cardiovasc. Qual. Outcomes*, 2:164-169).

In a particular embodiment, patients according to the invention are patients suffering from cardiac arrhythmia.

In another particular embodiment, patients according to the invention are patients suffering from arterial hypertension.

Use According to the Invention

In accordance with one aspect of the present invention, there is provided a process for inducing a decrease in cardiac arrhythmias, in particular in atrial fibrillation in a subject by use of a formulation or a combination as described herein.

In accordance with another aspect of the present invention, there is provided a process for inducing a decrease in the release of renin and/or blood pressure in a subject in need thereof, by use of a formulation or a combination as described herein.

The formulation or combination according to the invention is administered in an amount and in accordance with a dosage regimen that is effective for inducing a decrease in cardiac arrhythmias and/or blood pressure.

In another embodiment of the invention is provided a method for preventing, repressing or treating cardiac arrhythmias, in particular in atrial fibrillation, or arterial hypertension said method comprising administering in a subject in need thereof a therapeutically effective amount of a pharmaceutical formulation according to the invention.

According to another aspect, the formulations of the inventions could be used in different areas of medicine, where botulinum toxin only is used, i.e. not only for heart rhythm disorders treatment, since the main effect achieved by formulations of the invention is a blockage of neuromediator release from presynaptic terminal of nervous system and there are no principal histologic and cytologic differences between these synaptic compositions in other zones on human body.

According to one aspect, the formulations of the inventions are to be administered into intramyocardial GPs and epicardial fat pads.

Method of Preparation of Formulations of the Invention

The compositions of the invention can be prepared by mixing aqueous solutions of the components in predetermined proportions.

The advantage of a formulation of the invention is that it can be prepared from pure botulinum toxin type A or from a commercially available product based on botulinum toxin type A that allows the preparation of the required solution from the available components directly into clinical practice.

The formulations of the invention allow achieving an increase in the effect of botulinum toxin type A, while reducing side effects of systemic effect and produce immunoresistance (Substance of invention is using mucopolysaccharides to create mechanic protection of molecule and delay distribution of botulinum toxin molecule from targeted location). Molecules of chitosan are neutral and mechanically cover immunoreactive centers of botulinum toxin (Katherine Bowman et al., 2006, *Int. J. Nanomedicine*, 1(2): 117-128).

The advantage of the botulinum toxin composition of the invention is that—it would allow the reducing the necessary therapeutic dose, while increasing duration of drug effect as well as reduced side effects as undesirable denervation of unused muscles and development of systemic effects.

An additional advantage is the possibility of its preparation in the clinic directly from commercially available products enabling fine tuning the required properties, based on the target of application. Treatment of atrial fibrillation requires epicardial administration of the composition, where the priority property of chitosan is elongation release of botulinum toxin (botulinum toxin type A and chitosan in ratio of 1 to $4.4 \times 10^7$ by weight). Treatment of arterial hypertension requires renal intraarterial infusion of the composition, where the priority property of chitosan is an increase the adhesive properties of botulinum toxin for juxtaglomerular membrane (botulinum toxin type A and chitosan in ratio of 1 to $4 \times 10^5$ by weight).

With increasing ratio of active components (botulinum toxin type A/mucopolysaccharide of the invention) above $1:10^9$ by weight, there are difficulties with preparing therapeutically acceptable injectable preparations. For example, at a ratio of botulinum toxin type A/chitosan equal to $1:10^9$, and 40 U of botulinum toxin activity (equivalent to 1 ng), the necessary amount of chitosan is 1 gram that leads to an injection volume of 50 ml for clinically relevant concentrations of chitosan in 2% injection. This amount is excessive for therapy. With decreasing the ratio of active components in the composition (botulinum toxin type A/mucopolysaccharide) below $1:10^3$ by weight, the efficiency of the composition is significantly reduced and approaches the efficiency of the conventional formulations of botulinum toxin type A.

In another embodiment, is provided a medicinal kit comprising in compartmental form a first compartment or series of compartments comprising a composition of the invention and a second compartment or series of compartments comprising a syringe for injection with instructions for use.

Examples illustrating the invention will be described hereinafter in a more detailed manner and by reference to the embodiments represented in the Figures.

EXAMPLES

The invention is illustrated by the following examples.

Example 1. Preparation of Pharmaceutical Composition (No 1) Containing Botulinum Toxin Type A and Chitosan in Ratio of 1 to $4.4 \times 10^7$ by Weight To prepare the solution of botulinum toxin type A in all the experiments, the commercial preparations of botulinum toxin type A "Kseomin™" produced by MERZ PHARMA GmbH & Co., KGaA (Germany), registration number LSR-004746/08, auxiliaries, sucrose and human serum albumin, or "Lantoxs™" produced by Lanzhou Institute of Biological Products, (China), registration number LSR-001587/08, auxiliaries: gelatin, dextran and sucrose, were used.

In both cases, vials containing 100 units of botulinum toxin were used. In each vial 1000 μL of sterile saline were added. The resulting solutions were used for mixing with the chitosan solution obtained as described below. For the preparation of various chitosan solutions the drug "chitosol" produced by "Bioavanta" (Koltsovo, Novosibirsk Region, the degree of deacetylation of this chitosan is at least 90%, its average molecular weight of ~500 kDa and is prepared from crab shells) was used. To prepare 100 ml of 2.2% Chitosol solution, 1.1 g of siccine acid and 0.9 g of sodium chloride were dissolved in 100 ml of distilled water under heating in microwave oven. After complete dissolution of the acid and salt, 2.2 g of Chitosol was introduced by small portions before complete dissolution of every added portion was mixed and triturated by pallet.

Heating is carried out during 1 hour in microwave oven in the pulsed mode (⅙ time at a capacity of 600 W). To exclude formation of agglomerates the solution was subjected to treatment in an ultrasound cleaner during 10 minutes (after adding chitosan).

The pharmaceutical composition was prepared by mixing in 1 ml syringe equipped with a system Luer-Lok Tip, 100 μL of botulinum toxin type A solution (containing 10 U or 0.25 ng of botulinum toxin type A) and 400 μL of 2.75% chitosan solution (containing 11 mg of chitosan). The result was a liquid pharmaceutical composition comprising the following components:

| botulinum toxin type A | 20 IU/ml (0.5 ng/ml) |
|---|---|
| chitosan | 22 mg/ml |
| saline | 0.5 ml. |

Example 2. Preparation of Pharmaceutical Composition (No 2) Containing Botulinum Toxin Type A and Chitosan in Ratio of 1 to $1.76 \times 10^7$ by Weight The pharmaceutical composition was prepared by mixing in 2 ml syringe. The 100 units solution of botulinum toxin in 400 μL of saline was prepared and it was used (it contains 100 units, or 2.5 ng of botulinum toxin type A) for mixing with 1600 μL of 2.75% chitosan solution (containing 44 mg of chitosan).

The result was a liquid pharmaceutical composition comprising the following components:

| botulinum toxin type A | 50 IU/ml (1.25 ng/ml) |
|---|---|
| chitosan | 22 mg/ml |
| saline | up to 2 ml. |

Example 3. Preparation of Pharmaceutical Composition (No 3) Containing Botulinum Toxin Type A and Heparin in the Ratio of 1 to $1.6 \times 10^7$ by Weight (Comparative Formulation not of the Invention)

A Heparin solution with a concentration of 5000 IU/ml was used (production of Synthesis company, Kurgan, Russia, drug registration number P N000116/01). One unit of heparin is equal to 0.0077 mg of the International Standard heparin, i.e. 1 mg contains 130 IU (Pershyn G N, Gvozdeva E I Textbook of Pharmacology—Moscow: Medgiz, 1961-s.405).

The pharmaceutical composition was prepared by mixing 100 μL of botulinum toxin type A solution (containing 10 U or 0.25 ng of botulinum toxin type A), 104 μL of heparin solution containing 4 mg of heparin (~520 IU) and 500 μL of saline. The pharmaceutical composition comprising:

| botulinum toxin type A | 20 IU/ml (0.5 ng/ml) |
|---|---|
| heparin | 1040 IU/ml (8 mg/ml) |
| saline | 0.5 ml. |

Example 4. Preparation of Pharmaceutical Composition (No 4) Containing Botulinum Toxin Type A and Heparin in the Ratio of 1 to $5.3 \times 10^6$ by Weight (Comparative Formulation not of the Invention)

Analogously to Example 3 to obtain the pharmaceutical composition 300 μL of botulinum toxin type A solution (containing 30 U or 0.75 ng of botulinum toxin type A), 104 μL of heparin solution, containing 4 mg of heparin (~520 IU) and 500 μL of saline were mixed. The pharmaceutical composition comprising:

| botulinum toxin type A | 60 IU/ml (1.5 ng/ml) |
|---|---|
| heparin | 1040 IU/ml (8 mg/ml) |
| saline | up to 500 μL. |

Example 5. Preparation of Pharmaceutical Composition (No 5) Containing Botulinum Toxin Type A and Nadroparin in Ratio of 1 to $8 \times 10^6$ by Weight A solution of fraxiparine (nadroparin), (Sanofi Winthrop Industry, France, registration number P N012486/01) with a concentration of 9500 IU per mL was used for the experiment. One unit of action of low molecular heparin—nadroparin (average molecular weight—4000-7000 Da) has been accepted by us equal to one unit of heparin, i.e. 0.0077 mg.

For the preparation of the pharmaceutical composition 100 μL of botulinum toxin type A solution (containing 10 units or 0.25 ng of botulinum toxin type A), 27 μL of nadroparin solution, containing 2 mg of nadroparin (~260 IU) and saline up to 500 μL were mixed. The pharmaceutical composition comprising:

| | |
|---|---|
| botulinum toxin type A | 20 IU/ml (0.5 ng/ml) |
| nadroparin | 520 IU/mL (4 mg/ml) |
| saline | 0.5 ml. |

Example 6. Preparation of Pharmaceutical Composition (No 6) Containing Botulinum Toxin Type A and Nadroparin in Ratio of 1 to $2.67 \times 10^6$ by Weight For preparing a pharmaceutical composition 300 μL of botulinum toxin type A solution (containing 30 U or 0.75 ng of botulinum toxin type A), 27 μL of nadroparin solution containing 2 mg nadroparin (~260 IU) and 500 μL of saline were mixed. A pharmaceutical composition comprising:

| | |
|---|---|
| botulinum toxin type A | 60 IU/ml (1.5 ng/ml) |
| nadroparin | 520 IU/mL (4 mg/ml) |
| saline | 0.5 ml. |

Example 7. Preparation of a Pharmaceutical Composition (No 10) Containing Botulinum Toxin Type A and Chitosan Ratio of 1 to $2 \times 10^8$ by Weight Analogously to Example 1, a 5% solution of chitosan in saline was prepared. 10 ml of this solution was used to dissolve 100 U botulinum toxin type A (containing 100 ng or 2.5 units of botulinum toxin type A and 500 mg of chitosan). The result was a liquid pharmaceutical composition comprising the following components:

| | |
|---|---|
| botulinum toxin type A | 10 IU/ml (0.25 ng/ml) |
| chitosan | 50 mg/ml |
| saline | up to 10 ml |

Example 8. Preparation of a Pharmaceutical Composition Containing Botulinum Toxin Type A and Sodium Hyaluronate (Comparative Example, not of the Invention)

The pharmaceutical composition was prepared by mixing in 1 ml syringe equipped with a system Luer-Lok Tip, 100 μL of botulinum toxin type A solution (containing 20 U or 0.5 ng of botulinum toxin type A) and 400 μL of 1% sodium hyaluronate (containing 4 mg of sodium hyaluronate, Sigma-aldrich cat#53747). The result was a liquid pharmaceutical composition comprising the following components:

| | |
|---|---|
| botulinum toxin type A | 20 U/ml (0.5 ng/ml) |
| sodium hyaluronate | 10 mg/ml |
| physiological saline | make up to volume 0.5 ml. |

Example 9. Biological Tests of the Obtained Pharmaceutical Compositions

The effectiveness and safety of the pharmaceutical compositions of the invention (No 1-6) was performed in comparison with solutions of commercial preparations of botulinum toxin type A in saline and with pharmaceutical compositions comprising botulinum toxin type A and another mucopolysaccharide than chitosan or heparin (No 3 and 4) at the same dose, expressed in units.

The study was conducted within the framework of <<Good Laboratory Practice>>, in accordance with legal and ethical standards of animals' treatment, and the approval of the local ethics committee. For each experiment two groups of 10 experimental animals, Wistar rats, were used. Each group was injected in the right thigh with botulinum toxin type A, diluted in 0.9% sodium chloride solution (saline); pharmaceutical composition (No 1-6) was administered in the left thigh.

Anesthesia: ether

Injection volume: 0.5 ml in each thigh.

Method of administration: intramuscularly, three injection points (back, medial, lateral surface of the thigh), 0.16 ml in each.

Comparison of the formulations was carried out by assessing the reduction of thigh muscles in response to electrical stimulation. Threshold minimum change of intramuscular electrostimulation was compared in the course of time. Measurement of electrostimulation threshold was carried out intramuscularly using two sterile steel microelectrodes and ERA 300 device (Biotronic, USA). These microelectrodes, for the period of measurement, were temporarily inserted intramuscularly to a depth of about 4 mm in outer area of the mouse thigh, 10 mm away from each other. For example, if the minimum threshold of intramuscular electrostimulation was 4.0±0.2 V for composition No 1, and 2.0±0.12 V for the control, the physiological effect of the composition No 1 at the time of measurement is increased by 2 times compared with a commercial preparation of botulinum toxin.

Before injections, overall high activity (movement into rat coop) was observed in experimental animals of different groups.

During the first day after the injection procedure, the animals were exposed to residual phenomenon of drug sedation.

One week after injection, paralysis of lower limbs but movement due to the upper limbs in all rats was observed (clinical evidence of botulinum toxin action). Maximum thresholds of intramuscular electrical stimulation were for the compositions: No 1: 4.0±0.1 V (control 2.5±0.1 V, initially 1.5±0.1 V), No 2: 10.0±0.4 V (control 3.0±0.1 V, initially 1.0±0.1 V).

2 weeks after injection, paralysis of the lower limbs but movement due to the upper limbs in all rats was observed. Rats lost weight, and showed denial of food and water. Maximum thresholds of intramuscular electrical stimulation were for the compositions: No 1:6.0±0.3 V (control 2.5±0.2 V), No of 2: 10.0±0.5 V (control 2.3±0. 1).

After 3 weeks after injection, paralysis of the lower limbs but movement due to the upper limbs in all rats was observed. Dynamics of rat activity was increased. They drank actively and ate normally. Maximum thresholds of intramuscular electrical stimulation were for the compositions: No 1: 4.0±0.1 V (control 2.0±0.1 V), No 2: 5.0±0.2 V (control 1.8±0. 1).

After 4 weeks after injection, rats are objectively active and only paralysis of the lower extremities was still observed. Maximum thresholds of intramuscular electrical stimulation were for the compositions: No 1—4.0±0.2 V (control 2.0±0.12 V), No 2—5.0±0.3 V (control 2.0±0. 2).

For compositions No 3-6, the maximum effect was not observed during the first week after injection but was found during the second week; but the absolute value of the differences from the control was not as great as in the case of chitosan. Thus, for the comparative composition No 3. Maximum thresholds of intramuscular electrical stimulation during the second week were 1.8±0.1 V (control 2.3±0.1 V, 1.0±0.1 initially V), and for composition No 5: 2.2±0.1 V (control 1.5±0.1 V, initially 1.2±0.1 V) and comparative composition No 11: 1.5±0.1 V (control 2.6±0.2 V, initially 1±0.1 V).

Probably heparin quite firmly holds botulinum toxin type A, preventing its biological effects as compared with commercial preparations, whereas low molecular nadroparin, as opposed, enhances the action of botulinum toxin. It is further supported by the absence of significant effects for comparative formulation 4 as compared to formulation of the invention No 6.

The compositions of the invention were assessed for potential toxicity by histo-morphological study through histological examination of internal organs of experimental animals. Upon microscopic analysis of formalin-fixed and paraffin embedded tissue samples of liver, kidney, spleen, heart, skeletal muscle and brain, no morphological signs of pathological changes were found. Therefore, it was concluded, to the absence of damaging influence of botulinum toxin type A and pharmaceutical compositions of the invention at the testes doses, on tissues and organs of experimental animals.

Example 10. Investigation of Suppressing Induction of Atrial Fibrillation by Injection of a Pharmaceutical Composition Containing Botulinum Toxin Type A into Epicardial Fat Pad The test was conducted on a group of 10 dogs using a pharmaceutical composition No 2. Epicardial fat pads, containing the right-center ganglion plexus of the left atrium, were allocated through the right lateral thoracotomy.

In the group of experience (5 dogs), into each of the two right fat pads 1 ml solution of 50 U of botulinum toxin type A+chitosan (100 units of botulinum toxin type A-2 ml, composition No 2) were introduced. In the control group (5 dogs), in each of two fat pads 1 ml solution of 50 units of botulinum toxin type A+0.9% sodium chloride (100 IU of botulinum toxin type A—2 mL) were introduced.

Electrophysiological effects were evaluated after 1, 2, 3 and 4 weeks after injection, with and without cervical vagus nerve stimulation. Atrial fibrillation was achieved in both groups of dogs through cervical vagus nerve stimulation. This effect was blocked by the administration of the test and control solutions of botulinum toxin in the above described doses and areas in both groups. In the control group, the blockage of vagal effect disappeared on the 8$^{th}$ day after injection (the observation period). In the group of experience, the blockage of vagal effect persisted for more than 30 days after injection. Therefore, a temporary suppression of the cervical vagus nerve stimulation-induced atrial fibrillation by botulinum toxin injection into the epicardial fat pads of the left atrium was extended to more than 30 days (not less than 4 times) using composition of the invention No 2

These results indicates that using a botulinum toxin type A pharmaceutical composition of the invention, will increase the pharmacological activity of the toxin and reduce the necessary single dose to achieve the desired therapeutic effect which will allow to reduce botulinum toxin side effects. Similar results were obtained for composition No 6. Comparative formulations 4 and 11 were not able to achieve this effect (FIG. 1).

Example 11. Effects of Composition of the Invention in Comparison with Disaccharide Composition The comparison of the effectiveness and duration of the effect of pharmaceutical composition of the invention comprising botulinum toxin and chitosan (No 2) and a registered commercial composition comprising disaccharide (Comparative formulation No 11) was carried our as follows. Comparative formulation No 11 contains:
a) botulinum neurotoxin type A (20 U/ml (0.5 ng/ml))
b) stabilizing agent polysorbate 80 (0.02 vol. %)
c) sucrose, at a concentration 20 mM
d) buffer histidine to maintain the pH 5.5-7.5
e) physiological saline (saline of sodium chloride 0.9%) make up to volume 0.5 ml.

Figure 2:
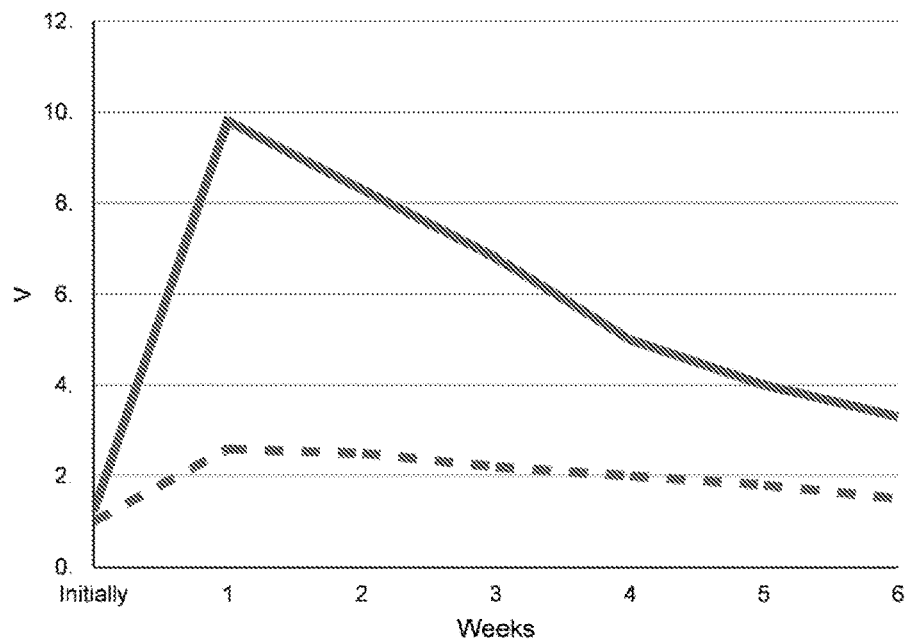
FIG. 2 represents the effect and its duration of a pharmaceutical composition of the invention as represented by the change in the electrostimulation threshold (measured in Volts) of rat's femoral muscles as compared to a composition containing disaccharide and botulinum toxin A, according to the description of the patent RU 2407541as described in Example 11.

Thresholds of intramuscular electrical stimulation of rat thigh muscle after injection was measured as described above.
Group 1—Formulation No 2
Group 2—Comparative formulation No 11
Results are represented on FIG. 2: Maximum thresholds of intramuscular electrical stimulation were for the Group 1: (9.8±0.3 V) vs Group 2: (2.6±0.1 V); Initially 1.2±0.1 V vs 1.0±0.1 V, respectively.

After 2 weeks: Group 1: 10.0±0.4 V vs Group 2:2.5±0.1 V.

After 4 weeks: Group 1: 5.0±0.2 V vs Group 2: 2.0±0.1 V.

After 6 weeks: Group 1: 3.3±0.2 V; stimulation threshold in the Group 2 decreased to close to the initial (1.5±0.1 V).

These data support that formulations of the invention comprising chitosan and botulinum toxin showed better efficacy and longer lasting effect than the registered commercial composition comprising disaccharide and botulinum toxin as described in patent RU 2407541.

Example 12. Effectiveness and Safety of Suppressing Atrial Fibrillation Inductibility Using the Chitosan+Botulinum Toxin Type A Composition (1:1.76×107) and Commercial Formulations Botulinum Toxin Prior animal studies suggest that botulinum toxin injection into the epicardial fat pads can suppress atrial fibrillation (AF) inducibility. The aim of the present study was to compare the efficacy and safety of endocardial botulinum toxin injection into epicardial fat pads and intramyocardial left atrial ganglionated plexi (GP) for preventing AF using chitosan+botulinum toxin type A (1:1.76×10$^7$) (formulation of the invention (No 2) and commercial formulations of Botulinum toxin.

Figure 4:
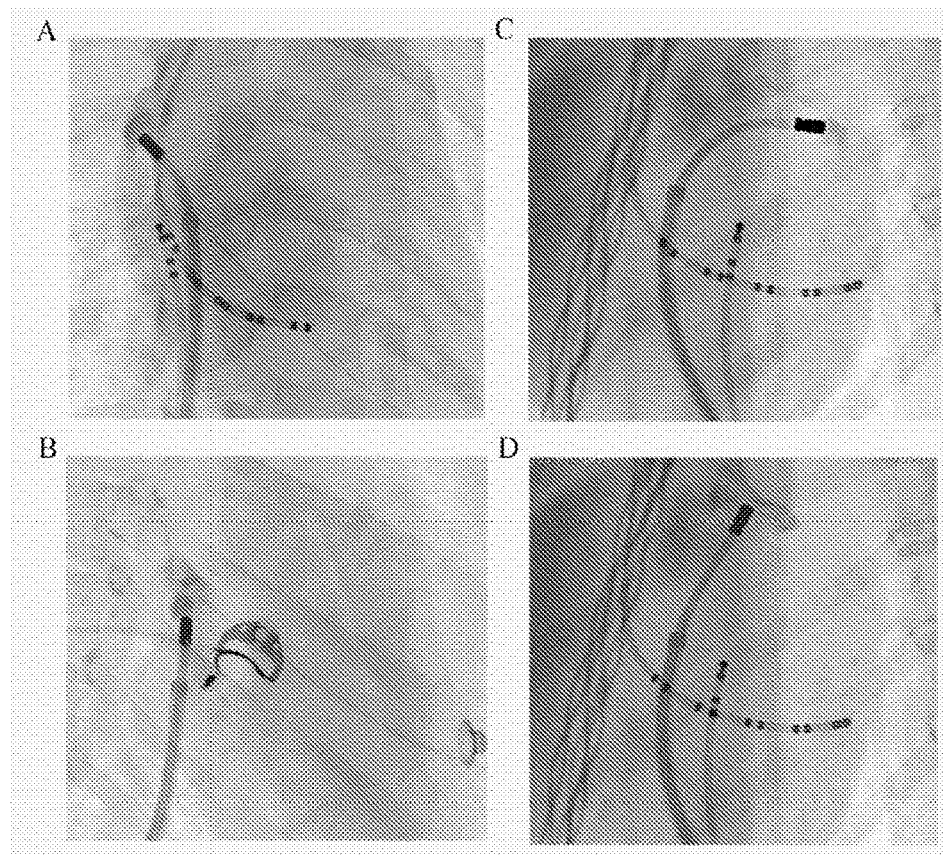
FIG. 4 shows pictures of a contrast injection [Visipaque™ (iodixanol)] into the epicardial fat pads containing the anterior right (A), inferior right (B) and superior left GP (C) as described in Example 12. Output needle of catheter into the pericardial space (D).

In 30 dogs, transvenous catheters were passed into the left atrium. Sites where vagal reflexes were evoked by high-frequency stimulation (HFS) were tagged on an electroanatomic mapping system and then designated for injection. Intramyocardial injections (10 U/0.2 mL at each) of botulinum toxin were administered at 7 sites per dog. In addition, 3 injections per dog were made into the epicardial fat pads containing the anterior right, inferior right and superior left GP (50 U/1 mL at each) also by endocardial approach (FIG. 4). The vagal reflexes by HFS and AF inducibility were evaluated before injections and then every 2 weeks until the return of all changes to baseline by precise catheter reposition and stimulation over the GP sites marked on the previously recorded map. 15 of 30 dogs were injected by chitosan+botulinum toxin composition ($1:1.76\times10^7$), other 15 of 30 dogs were injected by botulinum toxin (Xeomin, Germany).

Figure 5:
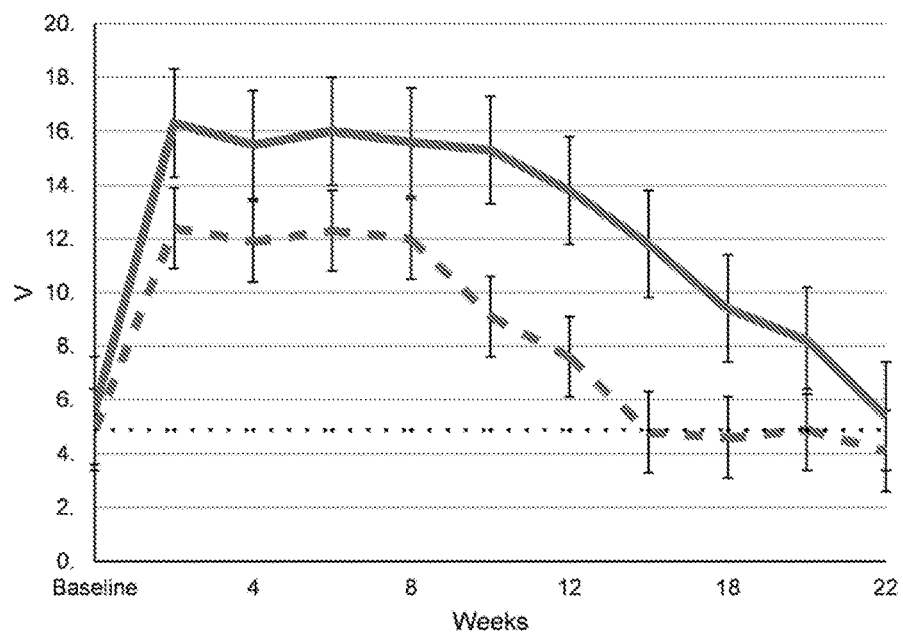
FIG. 5 shows the threshold of stimulation as measured by the change in the electrostimulation threshold (measured in Volts) of rat's femoral muscles that induced AF as described in Example 11. ( . . . baseline), ( - - - Xeomin), (—formulation No 2).

At 2 weeks after the procedure, all dogs demonstrated complete elimination of the vagal response, and then full recovery to baseline values at 14.7±1.5 weeks in group Xeomin and 20.1±1.8 weeks in group chitosan+botulinum toxin ($p<0.05$; (FIG. 5)). The threshold of stimulation that induced AF increased from 4.9±0.6 V at baseline to 12.4±2.5 V at 2 weeks in group Xeomin and from 5.6±1.2 V at baseline to 16.3±2.2 V, in group chitosan+botulinum toxin accordingly ($p<0.05$). No procedure-related complications occurred.

These data suggest that Botulinum toxin injection into intramyocardial GPs and epicardial fat pads by an endocardial approach was feasible and safe, and provided complete abolition of cardiac vagal responses and significant AF suppression. Chitosan+botulinum toxin type A composition ($1:1.76\times10^7$) is more effective and has prolonged duration of action than a commercial formulation of Botulinum toxin type A (Xeomin, Germany).

Example 13. Effectiveness and Safety of Arterial Hypertension Suppressing Using the Chitosan+Botulinum Toxin Type A Composition ($1:4.4\times10^7$), Composition ($1:1.76\times10^7$) and Commercial, Formulations Botulinum Toxin Prior in vitro studies suggest that botulinum toxin injection into the rat's kidney suppresses active renin release and leads to decrease of blood pressure (Mendez et al., 2013, *Am. J. Physiol. Renal. Physiol.* 304:F498-F504). The aim of the present study was to compare the efficacy and safety of botulinum toxin infusion into renal arteries for preventing arterial hypertension using formulations of the invention, in particular chitosan+botulinum toxin type A (formulation of the invention No 1, $1:4.4\times10^7$), chitosan+botulinum toxin type A (formulation of the invention No 2, $1:1.76\times10^7$) and commercial formulations of Botulinum toxin (Xeomin, Germany).

In 9 pigs, transvenous catheters were consequentially passed into the left and right renal artery. Intrarenal infusion (50 U/1 mL) of botulinum toxin was administered at each pig's kidney (for composition No 1: 3 pigs; composition No 2: 3 pigs; commercial formulation of Botulinum toxin: 3 pigs). 3 pigs were included in Placebo group with 1 ml of physiological saline (saline of sodium chloride 0.9%) infusion into each renal artery. All protocols were approved by the Institutional Animal Care and Use Committee in accord with the Guide for the Care and Use of Laboratory Animals. At 1 week after the procedure, all the kidneys were explanted. Kidneys were decapsulated and homogenized. The obtained cells were incubated in solution which contained 100 U/ml penicillin, 100 μg/ml streptomycin, and 5% fetal calf serum at 37° C./5% $CO_2$ in poly-D-lysine-coated plates (0.1 mg/ml). Cells were serum deprived for 2 h by replacing the medium with serum-free solution which contained 100 U/ml penicillin and 100 μg/ml streptomycin. Renin release was stimulated by increasing intracellular levels of cAMP with forskolin (10 μM) plus 3-isobutyl-1-methylxanthine (0.5 mM) for 1 h. Following treatment, the medium was centrifuged to remove cellular debris. Supernatants were collected in fresh tubes and stored at −20° C. until processing. Analysis of the stimulated renin content in the supernatant was performed by using a reagent Renin ELISA kit (R&D Systems, USA).

At the end of 1 week after infusion procedure, the following average values of Renin concentration (%) were measured in the supernatant samples: formulation of the invention No 1, ($1:4.4\times10^7$)–2.8±0.5%; formulation of the invention No 2, ($1:1.76\times10^7$)–1.5±0.2%; commercial formulations of Botulinum toxin (Xeomin, Germany)–4.2±1.2%; placebo group (saline of sodium chloride 0.9%)–4.8±1.4%. No procedure-related complications occurred.

These data suggest that Botulinum toxin infusion into renal arteries for preventing arterial hypertension was feasible and safe, and provided significant reduction in the release of renin which is a key enzyme in the process of blood pressure increasing. Chitosan+botulinum toxin type A composition No 2 ($1:1.76\times10^7$) is more effective than Chitosan+botulinum toxin type A composition No 1 ($1:4.4\times10^7$) and a commercial formulation of Botulinum toxin type A (Xeomin, Germany).

Example 14. Effects of Chitosan and Botulim Toxin Composition with Different Toxin to Chitosan, Weight Ratios Features allowing improving the effect of botulinum toxin action depending on the injection site were revealed while investigating an optimal ratio of chitosan+botulinum toxin. For higher content of chitosan, the elongation release function of the composition prevails. Higher contents of chitosan are suitable for administration of the composition into adipose tissue, where therapeutic botulinum toxin concentrations can be reached through a slow release.

In contrast, when the composition is administered into such target areas as renal artery and ventricular myocardium, where there is direct contact with the blood supply system, it is require achieving rapidly a therapeutic concentration and an increase of the exposure to botulinum toxin. This requirement is satisfied by reducing the quantitative ratio of chitosan, which in turn leads to prevailing adhesion function of the composition.

Figure 3:
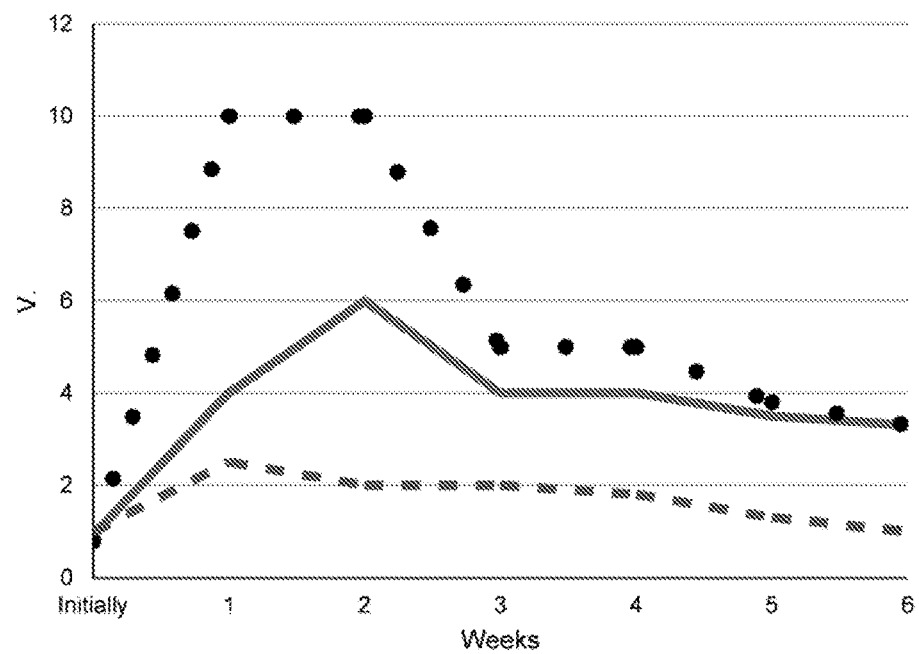
FIG. 3 shows the comparative effects of two pharmaceutical compositions of the invention at different concentrations of chitosan as represented by the change in the electrostimulation threshold (measured in Volts) of rat's femoral muscles with those of a commercial composition (Xeomin), as described in Example 13. (—Xeomin), (—Formulation No 1), (—Formulation No 2).

As it is shown on the FIG. 3, when the concentration of chitosan is increased in the formulations, i.e. when the weight ratio of botulinum toxin to chitosan is decreased in the composition (from $1:1.76\times10^7$ (No 2) to $1:4.4\times10^7$ (No 1) the botulinum toxin release rate and profile are also changed and accordingly effectiveness targeted on location is changed, while action duration varies slightly. Nevertheless, the effectiveness remains twice the one of a commercial formulation of botulinum toxin.

When endomyocardial injection is performed, botulinum toxin is more diluted as compared with botulinum toxin injection in epicardial fat pads. Accordingly, epicardial injections of chitosan+botulinum toxin need another concentration ratio (tends to $1:4.4\times10^7$), that allows to get good effectiveness and reduces risks of serious adverse events, whereas an endomyocardial injection needs a concentration ratio tending to $1:1.76\times10^7$ that allows getting therapeutic concentration in targeted location. This fact is confirmed by comparing the effectiveness of the concentration ratio $1:4.4\times10^7$ and $1:1.76\times10^7$ according to the procedure described in Example 12 (with intramyocardial injection only). At 2 weeks after the procedure, all dogs demonstrated complete elimination of the vagal response. The threshold of stimulation that induced AF increased from 5.1±0.8 V at baseline to 8.3±3.1 V at 2 weeks in group concentration ratio 1:4.4×10$^7$ and from 4.9±1.1 V at baseline to 15.8±2.4 V, in group concentration ratio accordingly 1:1.76×10$^7$ (p<0.05).

The invention claimed is:

1. A composition comprising botulinum neurotoxin type A and a mucopolysaccharide selected from the group consisting of chitosan having an average molecular weight (Mw) of about 100 kDa to about 1,000 kDa and nadroparin, and a physiologically acceptable excipient; wherein the weight ratio of botulinum neurotoxin type A to mucopolysaccharide is from about 1:10$^6$ to about 1:10$^8$.

2. A composition according to claim 1 wherein the mucopolysaccharide is chitosan.

3. The composition according to claim 2 wherein the chitosan has a deacetylation degree from about 85% to about 100%.

4. The composition according to claim 1 wherein the weight ratio of botulinum neurotoxin type A to mucopolysaccharide is from about 1:1.5×10$^7$ to about 1:5×10$^7$.

5. The composition according to claim 1 comprising the following components:

| | |
|---|---|
| botulinum neurotoxin type A | 1-200 IU/ml |
| mucopolysaccharide | 0.1-50 mg/ml |
| saline | 0.1-50 ml. |

6. The composition according to claim 1 comprising from about 20 to about 200 IU botulinum neurotoxin type A.

7. The composition according to claim 1 wherein the composition is a pharmaceutical formulation.

8. The composition according to claim 7 wherein the composition is an injectable formulation.

9. The composition according to claim 1 wherein the composition further comprises at least one antiarrhythmic substance of class I, II or III.

10. A method of treating atrial fibrillation or arterial hypertension in a subject in need thereof, such method comprising administering a composition according to claim 1 in said subject in need thereof.

11. A method according to claim 10, wherein the composition is to be administered into intramyocardial GPs, epicardial fat pads or renal artery.

12. A method according to claim 11, wherein the composition is to be administered into at least one epicardial fat pad; wherein the dose of botulinum toxin type A is 50 IU/ml.

13. A method according to claim 10 wherein the composition is to be administered in combination with at least one antiarrhythmic substance of class I, II or III.

14. A medicinal kit comprising in compartmental form a first compartment or series of compartments comprising a composition according to claim 1 and a second compartment or series of compartments comprising a syringe for injection with instructions for use.

* * * * *

UNITED STATES PATENT AND TRADEMARK OFFICE
CERTIFICATE OF CORRECTION

PATENT NO. : 10,258,673 B2  
APPLICATION NO. : 14/888511  
DATED : April 16, 2019  
INVENTOR(S) : Pokushalov et al.

Page 1 of 1

It is certified that error appears in the above-identified patent and that said Letters Patent is hereby corrected as shown below:

On the Title Page

Page 2, Other Publications, Line number 22, replace "Supresses" with --Suppresses--;

Page 2, Other Publications, Line number 25, replace "Artial" with --Atrial--;

In the Specification

At Column 1, Line number 34, after "Toxins" insert --,--;

At Column 13, Line number 67, after "No 2" insert --.--;

At Column 14, Line number 50, replace "(1:1.76×107)" with --1:1.76×10$^7$--;

At Column 16, Line number 26, replace "Botulim" with --Botulinum--;

At Column 16, Line number 27, replace "Chitosan," with --Chitosan--;

At Column 16, Line number 63, after "location." insert --¶--;

In the Claims

Claim 2, Column 17, Line number 14, replace "A" with --The--;

Claim 11, Column 18, Line number 15, replace "A" with --The--;

Claim 12, Column 18, Line number 18, replace "A" with --The--;

Claim 13, Column 18, Line number 21, replace "A" with --The--.

Signed and Sealed this  
Third Day of September, 2019

Andrei Iancu  
*Director of the United States Patent and Trademark Office*